United States Patent [19]

Druilhe et al.

[11] Patent Number: 5,690,941
[45] Date of Patent: Nov. 25, 1997

[54] **MOLECULES CONTAINING AT LEAST ONE PEPTIDE SEQUENCE CARRYING ONE OR SEVERAL EPITOPES CHARACTERISTIC OF A PROTEIN PRODUCED BY *P. FALCIPARUM* AT THE SPOROZOITE STAGE AND IN THE HEPATOCYTES**

[75] Inventors: Pierre Druilhe, Saint-Mandé; Claudine Guerin-Marchand, Paris, both of France

[73] Assignee: Institut Pasteur, France

[21] Appl. No.: 242,060

[22] Filed: May 13, 1994

Related U.S. Application Data

[63] Continuation of Ser. No. 104,597, Aug. 10, 1993, abandoned, which is a continuation of Ser. No. 758,724, Sep. 9, 1991, abandoned, which is a continuation of Ser. No. 507,215, Apr. 11, 1990, abandoned.

[30] Foreign Application Priority Data

Apr. 12, 1989 [FR] France .................... 89 04847

[51] Int. Cl.$^6$ .................... A61K 39/015; C07K 14/445
[52] U.S. Cl. .................... 424/272.1; 424/185.1; 424/268.1; 435/69.3; 530/300; 530/350; 530/395
[58] Field of Search .................... 424/184.1, 185.1, 424/269.1, 272.1; 530/300, 350, 395; 514/2, 8; 435/69.3

[56] References Cited

U.S. PATENT DOCUMENTS 5,112,749  5/1992  Brey, III et al. .................... 435/172.3

OTHER PUBLICATIONS

Weber et al, J. Biol. Chem., v. 263, n. 23, Aug. 15, 1988, pp. 11421–11425.
Sharma et al, Science, v. 229, Aug. 23, 1985, pp. 779–782.
Triglia et al, EMBO J, v. 6, n. 5, 1987, pp. 1413–1419.
Lal et al, J. Biol. Chem., v. 262, n. 7, Mar. 5, 1987, pp. 2937–2940.
Galinski et al, Cell, v. 48, Jan. 30, 1987, pp. 311–319.
Stryer, Biochemistry, W.H. Freeman & Co, San Francisco, 1975, pp. 14, 15 & 512.
Guerin–Marchand et al Nature 329 (1987) pp. 164–167.
Stahl et al PNAS 81 (1984) pp. 2456–2460.
Herrington et al Nature 328 (1987) pp. 257–259.
Guerin–Marchand et al., "A liver–stage–specific antigen of Plasmodium falciparum characterized by gene cloning", Nature 329: 164–167 (1987).
Stahl et al., "Differential antibody screening of cloned Plasmodium falciparum sequences expressed in *Escherichia coli*: Procedure for isolation of defined antigens and analysis of human antisera", Proc. Natl. Acad. Sci. USA 81: 2456–2460 (1984).
Herrington et al., "Safety and immunogenicity in man of a synthetic peptide malaria vaccine against Plasmodium falciparum sporozoites", Nature 328: 257–259 (1987).

Weber et al., "Primary structure of a *Plasmodium falciparum* malaria antigen located at the merozoite surface and within the parasitophorous vacuole", J. Biol. Chem. 263: 11421–11425 (1988).

Sharma et al., "Diversity of circumsporozoite antigen genes from two strains of the malarial parasite *Plasmodium knowlesi*", Science 229: 779–782 (1985).

Triglia et al., "The complete sequence of the gene for the knob–associated histidine–rich protein from *Plasmodium falciparum*", EMBO Jour. 6: 1413–1419 (1987).

Lal et al., "Structure of the gene encoding the circumsporozoite protein of *Plasmodium yoelii*", J. Biol. Chem. 262: 2937–2940 (1987).

Galinski et al., "The circumsporozoite gene of the *Plasmodium cynomolgi* complex", Cell 48: 311–319 (1987).

Lubert Stryer, (ed). Biochemistry, W.H. Freeman & Co., (San Francisco, 1975) pp. 14, 15, 512.

Gordon Langsley, "Paludisme: Vers Un Vaccin Multivalent", Biofutur (+Supp) 70: 23 (1988).

Druilhe et al., Biological Abstracts, vol. 78, Abstract No. 59971 (1984).

Szarfman et al., Biological Abstracts, vol. 86, Abstract No. 49103 (1988).

Guerin–Marchand et al., Nature, vol. 329, 164 (1987).

*Primary Examiner*—Thomas M. Cunningham
*Attorney, Agent, or Firm*—Finnegan, Henderson, Farabow, Garrett & Dunner, L.L.P.

[57] ABSTRACT

The invention relates to a polypeptide characterized in that it contains at least one peptide sequence carrying one or several epitopes characteristic of a protein produced at the sporozoite stage and in the hepatocytes infected by *P. falciparum*, this sequence comprising a sequence of from 10 amino acids to the maximal number of amino acids of the following peptide chain sequence:

Glu-Phe-Arg-Val-Ser-Thr-Ser-Asp-Thr-Pro-Gly-Gly-Asn-Glu-Ser-Ser-Ser-Ala-Ser-Pro-Asn-Leu-Ser-Gly-Ala-Arg-Glu-Lys-Lys-Asp-Glu-Lys-Glu-Ala-Ser-Glu-Gln-Gly-Glu-Glu-Ser-His-Lys-Lys-Glu-Asn-Ser-Gln-Glu-Ser-Ala-Asn-Gly-Lys-Asp-Asp-Val-Lys-Glu-Glu-Lys-Lys-Thr-Asn-Glu-Lys-Lys-Asp-Asp-Gly-Lys-Thr-Asp-Lys-Val-Gln-Glu-Lys-Val-Leu-Glu-Lys-Ser-Pro-Lys-Glu-Phe.

It also relates to the use of these polypeptides, as well as the nucleotide sequences coding for these polypeptides, in methods of in vitro diagnosis of malaria on a biological sample derived from the individual in whom the disease is to be detected.

9 Claims, 4 Drawing Sheets

GAATTCCGAGTAAGTACTAGTGATACTCCTGGAGGAAATGAATC
                           28
TTCAAGTGCTTTCCCCCAATTTATCTGGTCAGCAGAAAAAAGG

ATGAAAAAGAAGCTTCTGAACAAGGAGAAGAAAGTCATAAAAAA

GAAAATTCCCAAGAAAGCGCGAATGGTAAGGATGATGTTAAAGA

AGAAAAAAAACTAATGAAAAAAAGATGATGGAAAAACAGACAA

GGTTCAAGAAAGGTTCTAG

AAAAGTCTCCAAGGAATTC
242                 261
//

FIG. 1

NUCLEOTIDE SEQUENCE I
CCAAGAAAGCGCGAATGGTAAGGAT
(13/25)

NUCLEOTIDE SEQUENCE II
TTCTAGAAAAGTCTCCAAAGGAATT
(17/25)

FIG. 3

MOLECULES CONTAINING AT LEAST ONE PEPTIDE SEQUENCE CARRYING ONE OR SEVERAL EPITOPES CHARACTERISTIC OF A PROTEIN PRODUCED BY P. FALCIPARUM AT THE SPOROZOITE STAGE AND IN THE HEPATOCYTES

This application is a continuation application of Ser. No. 08/104,597, filed Aug. 10, 1993, now abandoned, which is a continuation of application Ser. No. 07/758,724, filed Sep. 9, 1991, now abandoned, which is a continuation of application Ser. No. 07/507,215, filed Apr. 11, 1990, now abandoned.

The parasites responsible for malaria in man, including in particular Plasmodium falciparum or Plasmodium vivax to mention only the principal ones among them, exhibit different morphologies in the human host and express different antigens depending on their localization in the organism of the infected host, The morphological and antigenic differences of these parasites in the course of their life cycles in man make it possible to define at least four distinct stages of development.

The very first stage of development of the parasite in man corresponds to the sporozoite form introduced into the blood of the host by bites of insect carriers of the parasite. The second stage corresponds to the passage of the parasite into the liver and to the infection of the hepatic cells in which the parasites develop to form the hepatic schizonts which, when they are mature (6th day after penetration of the sporozoites), release the hepatic merozoites as a result of fission, The third stage is characterized by the infection of the blood erythrocytes by the asexual forms (merozoites) of the parasites; this erythrocytic stage of development of the parasite corresponds to the pathogenic phase of the disease. The fourth stage corresponds to the formation of the forms with sexual potential (or gametocytes) which will become sexual forms or extra-cellular gametes in the mosquito.

It is known that numerous studies have been undertaken to isolate from strains of parasites which are infectious for a human host polypeptide fractions in order to provide an in vitro diagnosis of malaria by detection of the corresponding antibodies, on the one hand, and in order to attempt to vaccinate against malaria, on the other.

For example, banks of cloned cDNAs derived from the sporozoites of Plasmodium falciparum have been set up by Enea et al, Science, 225, 628(1984). It was recognized that these banks comprised clones capable of expressing immunogenic polypeptides containing repetitive units of 4 amino acids specific for the circumsporozoite antigen (of P. falciparum).

However, little work has been carried out on the hepatic forms of the parasites responsible for malaria. The morphology of the hepatic forms was described for the first time in 1948 on the basis of biopsies on infected human volunteers (Trans. Roy. Soc. Trop. Med. Hyg., 41, 785 (1948). It was possible to describe a specific antigen of the hepatic stage of P. falciparum in the liver of South American monkeys insensitive to the blood forms of the parasite but in which the hepatic forms can develop (Am. J. Trop. Med. Hyg., 33, 336 (1984)).

The detection of the localization of the specific antigens of the liver was performed by means of immunofluorescence throughout the stages of maturation of the schizont. They are localized at the periphery of the parasite 5 to 40 microns in size; subsequently, they are distributed between the cytomeres or bundles of merozoites when the schizonts attain between 50 and 100 microns. They are distinct from the surface antigens of the sporozoites and the antigens shared by the schizonts of the blood and the liver which give an immunofluorescent image in the interior of the parasite.

Although it has since been possible to cultivate the hepatic forms of P. falciparum in human hepatocytes (Science, 227, 440 (1985)), the low yield of sporozoites which are transformed into manure forms of the parasite by the in vitro and in vivo culture methods does not permit biochemical analysis of the antigens produced at the hepatic stage.

It has also been observed that individuals suffering from malaria possess a very high titer of antibodies directed against the hepatic antigens. These hepatic antigens seem to be very powerful immunogens, among the most powerful of all of the antigens synthesized at the various stages of development of the parasite. On the other hand, the titer of antibodies directed against the forms of the blood stages of the parasite is sometimes very low, and consequently the diagnosis carried out on the basis of antigens specific for the blood stages can sometimes be falsely negative.

One of the aims of the present invention is precisely that of making possible the in vitro diagnosis of the infection of an individual by P. falciparum under more sensitive conditions than the present methods allow.

Another subject of the invention is novel compositions for the vaccination of humans against the malaria caused by P. falciparum.

The invention relates more particularly to molecules, polypeptides, or peptide or polypeptide compositions, characterized by the presence in their structure of one or more peptide sequences carrying one or more epitopes characteristic of the protein either present on the surface of the sporozoites or resulting from the infectious activity of P. falciparum in the hepatic cells.

One molecule expressed specifically during the hepatic phase has been identified by screening a bank of genomic DNA cloned in an expression vector with polyclonal sera (Guerin-Marchandet al.; Nature, 329, 164 (1987)). This LSA (Liver Stage Antigen) molecule consists of repeating units of 17 amino acids and seems to be very immunogenic under the natural conditions of exposure to the disease.

The polypeptide molecule which is the subject of the present invention differs from it by the absence of repetitions in the sequence recognized by antibodies, and by its expression at both the sporozoite stage and the hepatic stage.

BRIEF DESCRIPTION OF THE DRAWINGS

In what follows reference will be made to the drawings in which

FIG. 1 shows the amino acid sequence of the polypeptide of 87 amino acids characteristic of the sporozoite forms and of the hepatic forms of P. falciparum;

FIG. 3 represents the immunoblot, from an extract of sporozoites (NF 54 strain) of the parasitic protein comprising the polypeptidic sequence of the invention (fourth column; polypeptide of 70 Kd designated by DG 671 or SALSA) with respect to several controls: total serum (SH12 and SH15), monoclonal antibodies directed against the repetitive tetrapeptide of the circumsporozoite protein (Mab) anti-LSA antibody (DG 307).

Figure 2:
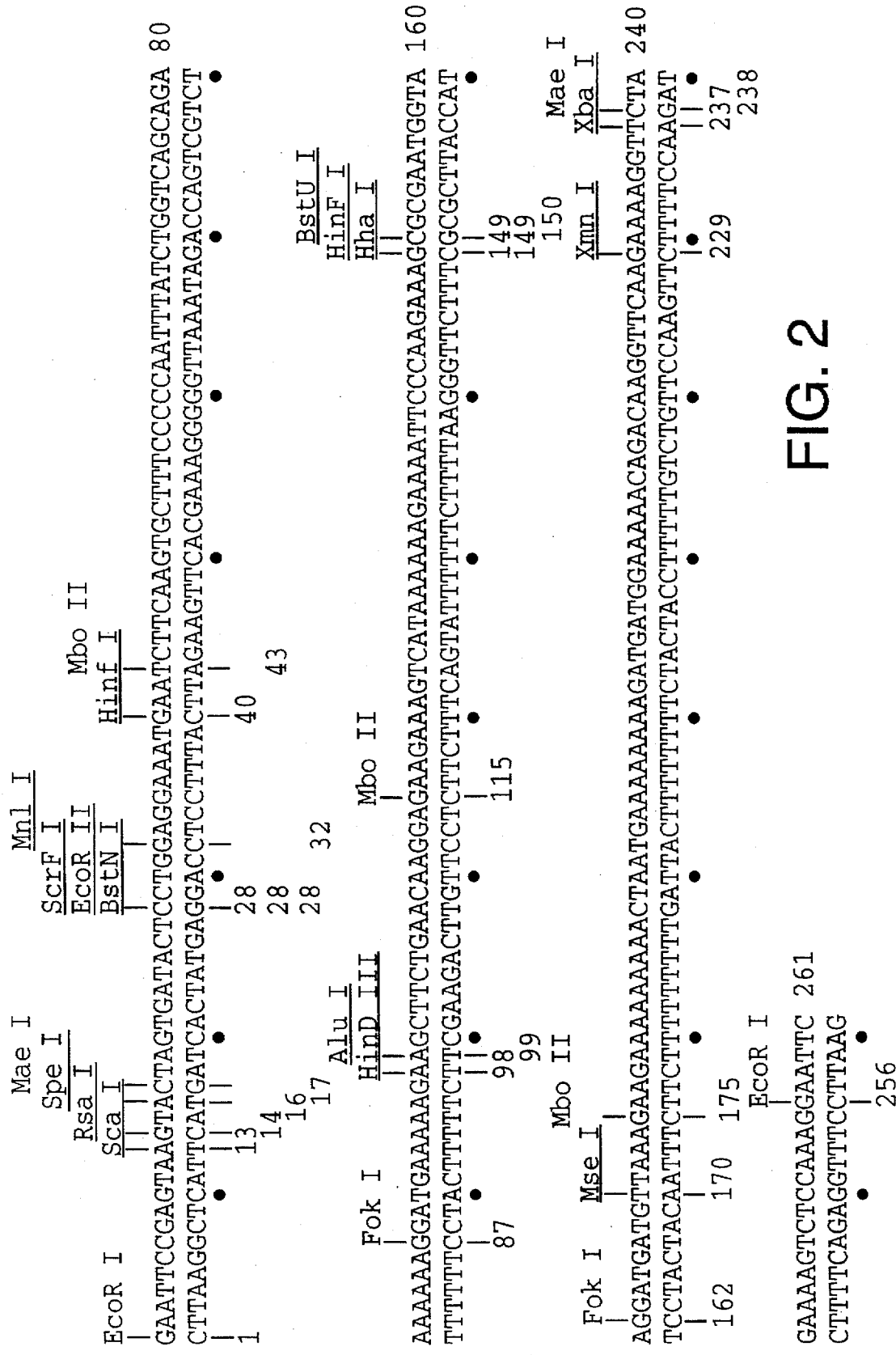
FIG. 2 presents the nucleotide sequences I and II derived from the sequence of FIG. 1 which can be used both as DNA primers or as probes.

A polypeptide according to the invention is essentially characterized in that it contains at least one peptide sequence carrying one or several epitopes characteristic of a protein produced at the sporozoite stage and in the hepatocytes infected by P. falciparum, this sequence comprising a sequence of from 10 amino acids to the maximum number of amino acids of the following peptide sequence:

Glu—Phe—Arg—Val—Ser—Thr—Ser—Asp—Thr—Pro—Gly—Gly—Asn—
1                                                                                    13

Glu—Ser—Ser—Ser—Ala—Ser—Pro—Asn—Leu—Ser—Gly—Ala—Arg—
14                                                                                   26

Glu—Lys—Lys—Asp—Glu—Lys—Glu—Ala—Ser—Glu—Gln—Gly—Glu—
27                                                                                   39

Glu—Ser—His—Lys—Lys—Glu—Asn—Ser—Gln—Glu—Ser—Ala—Asn—
40                                                                                   52

Gly—Lys—Asp—Asp—Val—Lys—Glu—Glu—Lys—Lys—Thr—Asn—Glu—
53                                                                                   65

Lys—Lys—Asp—Asp—Gly—Lys—Thr—Asp—Lys—Val—Gln—Glu—Lys—
66                                                                                   78

Val—Leu—Glu—Lys—Ser—Pro—Lys—Glu—Phe.
79                                        87 and in which "Leu" is leucine, "Ser" is serine, "Lys" is lysine, "Glu" is glutamic acid, "Gln" is glutamine, "Asp" is aspartic acid, "Phe" is phenylalanine, "Val" is valine, "Thr" is threonine, "Pro" is proline, "Gly" is glycine, "Asn" is asparagine, "Ala" is alanine, "Ile" is isoleucine, "Trp" is tryptophan, "His" is histidine, "Leu" is leucine, and "Arg" is arginine.

In the first instance, the invention relates to the monomeric peptides containing the unique peptide sequence of 87 amino acids corresponding to the formula shown above, and the terminal amino acids of which possess free amino and carboxylic termini respectively, or oligomers containing in particular multiples of the above-mentioned peptide sequence of 87 amino acids.

The invention also relates to the polypeptide of 87 amino acids itself, characterized by the above-mentioned sequence of amino acids.

This peptide sequence of 87 amino acids possesses the property of being recognized by antibodies recognizing the sporozoite and hepatic stages of P. falciparum; this sequence of 87 amino acids is not recognized by antibodies recognizing the blood (erythrocytic) stages of P. falciparum.

Another subject of the invention is any peptide sequence derived from the above-mentioned sequence of 87 amino acids and consisting of a sequence of 5, and preferably 10 to 86, amino acids included in the above-mentioned peptide sequences of 87 amino acids. These peptide sequences possess antigenic properties similar to those described above for the polypeptide of 87 amino acids.

A procedure for the selection of a peptide sequence of the Invention consists of verifying that this sequence is recognized by human immune sera derived from individuals who have been infected by P. falciparum.

As examples of peptide sequences of the invention, mention should be made in particular of the polypeptides, delimited respectively by the amino acids located at the positions 1 to 5, 20 to 50, 52 to 65, and 72 to 80 of the above-mentioned peptide sequence.

Two particularly interesting peptide sequences, hereafter designated by SALSA1 and SALSA2, are represented by the following amino acid sequences:

1-SALSA1: Ala-Arg-Glu-Lys-Lys-Asp-Glu-Lys-Glu-Ala-Ser-Glu-Gln Gly-Glu-Glu-Ser-His-Lys-Lys-Glu-Asn-Ser-Gln-Glu-Ser Ala, or are represented in the following manner:

AREKKDEKEASEQGEESHKKENSQESA

2-SALSA2: Asn-Gly-Lys-Asp-Asp-Val-Lys-Glu-Glu-Lys-Lys-Thr-Asn-Glu-Lys-Lys-Asp-Asp-Gly-Lys-Thr-Asp-Lys-Val-Gln-Glu-Lys-Val-Leu-Glu-Lye-Ser-Pro-Lys-Glu-Phe, or are also represented in the following manner:

NGKDDVKEEKKTNEKKDDGKTDKVQEKV-LEKSPKEF

Generally speaking, the invention relates to any polypeptide containing from 10 to 87 amino acids described above, end contained within the amino acid sequence shown in FIG. 1.

It is obvious that the free reactive functions which certain amino acids entering into the composition of the polypeptides according to the invention are likely to possess, in particular the free carboxyl groups carried by the Glu groups or the C-terminal amino acid, on the one hand, and/or the free groups carried by the N-terminal amino acid or by amino acids within the peptide chain, for example Lys, on the other, may be modified provided that this modification does not lead to a change in the antigenic properties, or possibly immunogenic properties, of the whole polypeptide. The molecules thus modified naturally enter into the framework of the protection given to the invention by the Claims. These carboxyl functions are possibly acylated or esterified.

Other modifications also enter into the framework of the invention. In particular, the amino or ester functions, or both at once, of the terminal amino acids may themselves be involved in linkages with other amino acids. For example, the N-terminal amino acid may be linked to a sequence comprising one to several amino acids corresponding to a part of the C-terminal region of another peptide conforming to the definition which was given above, or vice versa.

It will also be obvious that any peptide sequence resulting from the modification, by substitution and/or by addition and/or suppression of one or more amino acids, of the peptide sequence of 87 amino acids, or of a peptide sequence according to the invention, enters into the framework of the protection given to the invention by the Claims, provided that this modification does not impair the antigenic or immunogenic properties of the said polypeptide, in particular when these immunogenic properties have been adequately reinforced, for example by combination of the polypeptide with a suitable immunological adjuvant (for example a muramylpeptide) or by coupling with a carrier molecule of higher molecular weight (for example a serum albumin or a poly-lysine) or a toxin of the tetanus type or another antigen of *P. falciparum*.

More generally, the invention relates to any polypeptide characterized by the presence in its structure of one or more peptide sequences exhibiting immunological cross-reactions with all or part of the peptide sequence corresponding to the preceeding formula or peptide sequence according to the invention, towards antibodies induced by this latter in vivo.

The invention also relates to any sequence of nucleotides coding for a polypeptide of the invention.

The subject of the invention is more particularly the polypeptide of 87 amino acids shown in FIG. 1, and a nucleotide sequence consisting of 261 nucleotides which encodes the above-mentioned polypeptide.

The invention also relates to the nucleotide sequences coding for peptide sequences of the invention. As examples, mention should be made of the nucleotide sequences delimited respectively by the nucleotides located at the positions 1 to 45, 60 to 150, 156 to 195, and 216 to 240 of the nucleotide sequence coding for the polypeptide of FIG. 1.

The invention also relates to any sequence of nucleotides coding for a polypeptide identical or similar both from the point of view of structure and antigenic properties to those of the invention, this sequence being capable of hybridizing with the nucleotide sequence which encodes the polypeptide of FIG. 1, or the sequence complementary to this latter, under the following conditions:

pre-treatment (pre-hybridization) of the nitrocellulose filter supporting the nucleic acid fragment to be tested with the hybridization buffer (composed of 6×SSC, 2.5% milk, 0.5% SDS), this operation being carried out at 65° C. for 1 hour;

replacement of the hybridization buffer in contact with the support on which the nucleic acid fragment is then bound, by a hybridization buffer of the same composition (containing, in addition, denatured salmon DNA), and addition of the sequence of FIG. 1 as probe, in particular radioactively labelled, and denatured beforehand by a treatment at 100° C. for 5 minutes;

incubation of the said nucleic acid fragment bound to the support in this incubation buffer with the sequence of FIG. 1 at 65° C. for a duration of 16 to 24 hours, removal of the buffer containing the unbound probe by 3 successive washings of 5 minutes each with 2×SSC, 0.1% SDS at 65° C., followed by 3 successive washings of 5 minutes each with 0.1×SSC, 0.1% SDS at 65° C.

It should be recalled that 1×SSC is constituted by 0.15M of NaCl and 0.01M of sodium citrate, pH 7; SDS is sodium dodecyl sulfate.

Another subject of the invention is any recombinant nucleic acid containing at least one nucleic acid sequence of the invention, inserted into a nuclear acid heterologous with respect to the said sequence of nucleotides.

The invention relates more particularly to a recombinant nucleic acid such as that defined above, in which the sequence of nucleotides of the invention is preceded by a promoter (in particular an inducible promoter) under the control of which the transcription of the said sequence is capable of being brought about and, if necessary, followed by a sequence coding for termination signals of transcription.

The invention relates to any recombinant vector utilized in particular for the cloning of a nucleotide sequence of the invention, and/or the expression of the polypeptide encoded in this sequence, and characterized in that it contains a recombinant nucleic acid, such as that defined above, in one of its sites which is not essential for its replication.

As examples of the above-mentioned vector, mention may be made of plasmids, cosmids or phages.

In this respect, the invention relates more particularly to the plasmid DG671 deposited with the Collection Nationale de Cultures de Microorganismes (C.N.C.M.), Institut Pasteur, 28 rue du Docteur Roux, 75724 PARIS CEDEX 15, under the accession number I-855 on Mar. 31, 1989.

Another subject of the invention is a procedure for the preparation of a polypeptide of the invention by transformation of a cell host with the aid of a recombinant vector of the above-mentioned type, followed by the placing in culture of the cell host thus transformed, and of the recovery of the polypeptide from the culture medium.

Thus, the invention relates to any cell host transformed by a recombinant vector such as described above, and comprising the elements of regulation making possible the expression of the sequence of nucleotides coding for a polypeptide according to the invention.

The subject of the invention is more particularly primers of DNA (or RNA) which can be used in the context of the synthesis of nucleotide sequences and/or polypeptide sequences according to the invention, by the technique of PCR (Polymerase Chain Reaction) as described in the U.S. Pat. Nos. 4,683,202 and 4,683,195 and the European patent application No. 200.362 (PCR: chain amplification of DNA).

The invention relates to any DNA or RNA primer, characterized in that it is constituted of about 10 to 25 nucleotides, identical with the first 10 to 25 nucleotides of the sequence of nucleotides coding for a peptide sequence according to the invention or identical with the last 10 to 25 nucleotides of the said sequence.

The invention also relates to any DNA or RNA primer, characterized in that it is constituted by about 10 to 25 nucleotides complementary to the first 10 to 25 nucleotides of the nucleotide sequence coding for a peptide sequence according to the invention or complementary to the last 10 to 25 last nucleotides of the said sequence of nucleotides.

Another subject of the invention is any DNA or RNA primer, characterized in that it is constituted of about 10 to 25 nucleotides capable of hybridizing with the first 10 to 25 nucleotides or with the last 10 to 25 nucleotides of the said sequence of nucleotides coding for a polypeptide of the invention under the conditions of hybridization defined above.

Thus, the present invention relates more particularly to a procedure for the preparation of a polypeptide of the comprising the following steps:

if necessary, the prior amplification according to the PCR technique of the quantity of sequences of nucleotides coding for the said polypeptide with the aid of two DNA primers selected such that one of these primers is identical with the first 10 to 25 nucleotides of the nucleotide sequence coding for the said polypeptide, whereas the other primer is complementary to the last 10 to 25 nucleotides (or hybridizes with these last 10 to 25 nucleotides) of the said nucleotide sequence, or inversely, such that one of these primers is identical with the last 10 to 25 nucleotides of the said sequence, whereas the other primer is complementary to the first 10 to 25 nucleotides (or hybridizes with the first 10 to 25 nucleotides) of the said nucleotide sequence, followed by the introduction of the said sequences of nucleotides thus amplified into an appropriate vector, the placing in culture in a suitable culture medium of a cell host previously transformed by a suitable vector containing a nucleic acid according to the invention comprising the nucleotide sequence coding for the said polypeptide, and the recovery from the above-mentioned culture medium of the polypeptide produced by the said transformed cell host.

As examples of DNA or RNA primers according to the invention, mention may be made of the sequences I and II shown in FIG. 2.

The peptides according to the invention can be prepared by standard techniques used in the field of peptide synthesis. This synthesis can be carried out in homogeneous solution or on a solid phase.

For example, recourse may be had to the method of synthesis in homogeneous solution described by HOUBEN-WEYL in the monograph entitled "Methoden der Organischen Chemie" (Methods in Organic Chemistry) edited by E. Wunsch, vol. 15-I and II., THIEME, Stuttgart 1974.

This method of synthesis consists of condensing successive amino acids two eta time in the required order, or of condensing amino acids with fragments already formed and already containing several amino acids in the appropriate order or also of condensing several fragments previously prepared in this way, it being understood that care will have been taken to protect beforehand all the reactive functions presented by these amino acids or fragments with the exception of the amino function of one and the carboxyl function of the other which are necessarily involved in the formation of the peptide bonds, in particular after activation of the carboxyl function, according to the methods well-known in the synthesis of peptides. As an alternative, recourse may be had to coupling reactions making use of standard coupling reagents of the carbodiimide type such as, for example, 1-ethyl-3-(3-dimethyl-aminopropyl)-carbodiimide. When the amino acid used possesses an additional acidic function (particularly in the case of glutamic acid), these functions must be protected, for example, by t-butyl ester groups.

In the case of step-wise synthesis in which amino acids are added one at a time, the synthesis starts preferably by the condensation of the C-terminal amino acid with the amino acid which corresponds to the neighbouring amino acid in the desired sequence and it continues in this manner until the N-terminal amino acid has been condensed. According to another preferred method of the invention, described by Merrifield et al., "Solid Phase Peptide Synthesis," *J. Am. Soc.*, 45, 2149 (1961)

In order to prepare a peptide chain according to the procedure of Merrifield et al., recourse is had to a very porous polymeric resin to which is attached the first amino acid, the C-terminal residue of the chain. This amino acid is attached to the resin through its carboxyl group and its amino function is protected, for example by the t-butoxycarbonyl group.

When the first C-terminal acid is thus fixed to the resin, the projecting group of the amino function is removed by washing the resin with an acid.

In the case in which the protecting group of the amino function is the t-butoxycarbonyl group, it can be removed by treatment of the resin with the aid of trifluoroacetic acid.

Subsequently, the second amino acid, which furnishes the second amino acid of the desired sequence counting from the C-terminal amino acid residue, is coupled to the deprotected amino function of the C-terminal amino acid, the first amino acid attached to the resin. The carboxyl function of this second amino acid is preferably activated, for example by means of dicyclohexylcarbodiimide and the amino function is protected, for example by means of t-butoxycarbonyl.

In this way, the first part of the desired peptide chain, which consists of two amino acids, the terminal amino function of which is protected, is obtained. The amino function is deprotected as previously described and subsequently the third amino acid is coupled under conditions analogous to those used for the addition of the second C-terminal amino acid.

In this way, each of the amino acids which will constitute the peptide chain is coupled one after the other to the deprotected amine group of the portion of the peptide chain already formed and which is attached to the resin.

When the desired peptide chain has been formed in its entirety, the protecting groups are removed from the different amino acids constituting the peptide chain and the peptide is cleaved from the resin with the aid of hydrogen fluoride, for example.

The invention also relates to water-soluble oligomers of the above-mentioned monomeric peptides. Oligomerization can bring about an increase of the immunogenicity of the monomeric peptides according to the invention. It may be mentioned that these oligomers may, for example, contain from 2 to 10 monomeric units, without implying that this number is to be considered as limiting.

For the preparation of the oligomers, recourse may be had to any method of polymerization commonly used in the field of peptides, this polymerization reaction being conducted until an oligomer or polymer containing the required number of monomeric units for the acquisition of the desired immunogenicity is obtained.

One method of oligomerization or polymerization of the monomer consists in the reaction of the latter with a cross-linking agent such as glutaraldehyde.

Recourse may also be had to other methods of oligomerization or coupling, for example that involving the successive coupling of monomeric units through their carboxyl and amino terminal functions in the presence of homo- or hetero-bifunctional coupling agents.

The invention also relates to the conjugates obtained by covalent coupling of the peptides according to the invention (or the above-mentioned oligomers) to physiologically acceptable and non-toxic carrier molecules (natural or synthetic) by the intermediary of complementary reactive groupings carried respectively by the carrier molecule and the peptide. Examples of appropriate groupings are illustrated in what follows.

As examples of carrier molecules or macromolecular supports entering into the constitution of the conjugates according to the invention, mention should be made of naturally occurring proteins such as tetanus toxoid, ovalbumin, serum albumins. hemocyanins, the PPD of tuberculin (PPD="Purified Protein Derivative") etc. . .

As examples of synthetic macromolecular supports, mention should be made for example of the polylysines or the poly(D,L-alanine)-poly(L-lysine).

Other types of macromolecular supports which can be utilized are mentioned in the literature; usually they have a molecular weight higher than 20,000.

In order to synthesize the conjugates according to the invention, recourse may be had to known procedures such as that described by Franz et al., *Infect. and Immunity,* 33, 193 (1981), or that described by Kauffman, *Applied and Envi-* ronmental Microbiology, 42, 611 (1981), by using the peptide and the appropriate carrier molecule.

In practice and without implying any restriction, the following compounds can advantageously be used as coupling agents; glutaraldehyde, ethyl chloroformate, water-soluble carbodiimides [N'(3-dimethylamino-propyl) carbodiimide HCl], diisocyanates, bis-diazobenzidine, di- and trichloro-s-triazines, cyanogen bromide, as well as the coupling agents mentioned by Avrameas et al., *Scand. J. Immunol.,* 8, 7 (1978).

It is possible to have recourse to any coupling procedure implicating, on the one hand, one or more reactive functions of the peptide and, on the other, one or more reactive functions of the support molecules. Advantageously, these reactive functions are the amino and carboxyl functions, which can give rise to a coupling reaction in the presence of a coupling agent of the type of those used in the synthesis of proteins, for example 1-ethyl-3-(3-dimethylamino propyl) carbodiimide. N-hydroxybenzotriazole, etc. . . It is also possible to have recourse to glutaraldehyde, in particular when it is required to link together amino groups carried, respectively, by the peptide and the support molecule.

The nucleic acids of the invention can be prepared either by a chemical process or by other processes.

An appropriate embodiment for the preparation of the nucleic acids comprising a maximum of 200 nucleotides (or 200 pb when they are bicatenary nucleic acids) of the invention, comprises the following steps:

DNA synthesis with the use of the automated method of β-cyanyl-ethyl-phosphoramidite described in *Bioorganic Chemistry* 4, 274–325 (1986), cloning the nucleic acids which are thus obtained in an appropriate vector and recovering the nucleic acids by hybridization with an appropriate probe.

An embodiment for the preparation by chemical route of nucleic acids of a length higher than 200 nucleotides (or 200 pb, when they are bicatenary nucleic acids) of the invention comprises the following steps:

assembling oligonucleotides which have been chemically synthesized, comprising different restriction sites at their extremities, the sequences of which are compatible with the sequence of the amino acids of the natural polypeptide according to the process described in *Proc. Natl. Acad. Sci. USA,* 80; 7461 (1983), cloning nucleic acids which are thus obtained in an appropriate vector and recovering the sought nucleic acid by hybridization with an appropriate probe.

The nucleic acids of the invention can also be prepared according to the following manner:

incubating genomic DNA, isolated from a strain of *P. falciparum* with DNAase I, then adding EDTA and purifying by extraction with a mixture of phenol chloroformisoamylic alcohol (25/24/1) then by ether, treating DNA which has thus been extracted with EcoRI methylase in the presence of DTT, and purifying by extraction such as above described, incubating DNA which has thus been purified with the 4 triphosphate desoxynucleotides dATP, dCTP, dGTP, dTTP in the presence of T4 DNA polymerase and DNA aligase of *E. coli,* then purifying according to the above mentioned method, cloning the nucleic acids which have thus been obtained in an appropriate vector and recovering the sought nucleic acids by means of an appropriate probe.

The nucleotidic probes which are used for the recovery of the sought nucleic acid in the above mentioned process are generally constituted from 40 to 200 nucleotides of the nucleotidic sequence represented on FIG. 1, or of its complementary sequence, and are liable to hybridize with the sought nucleic acids in the above mentioned hybridization conditions.

The synthesis of these probes is carried out according to the automatized method of β-cyanylphosphoramidite described in *Bioorganic Chemistry* 4, 274 (1986).

In addition to the fact that they are present at the sporozoite stage, the polypeptides according to the invention also possess antigenic properties characteristic of specific antigens of the hepatic stage of the development of *P. falciparum*.

In fact, as will be more particularly described with the aid of examples of polypeptide molecules according to the invention in the detailed description which follows, the polypeptides according to the invention react specifically with the antibodies directed against the hepatic antigens produced by *P. falciparum* and also with the antibodies directed against other antigens of the sporozoite of *P. falciparum,* but not with the antibodies directed against antigens produced at other stages or by other species of Plasmodium.

These polypeptides according to the invention thus recognize specifically the antibodies produced by the immune system of an individual infected by *P. falciparum* under the effect of the antigens of the hepatic stage, the strongly immunogenic character of which has already been mentioned.

Thus, the possibility of producing in large amounts molecules according to the invention as well as their properties of specific recognition of the most actively produced antibodies in the course of the infection of an individual by *P. falciparum,* make the said molecules the reagents of choice for the in vitro diagnosis of malaria in an individual infected by *P. falciparum.*

Thus, the invention relates to an in vitro detection procedure for antibodies which can be correlated with malaria resulting from the infection of an individual by *P. falciparum* in a tissue or biological fluid likely to contain them, this procedure comprising the placing in contact of this tissue or biological fluid with a molecule according to the invention under conditions permitting an in vitro immunological reaction between the said molecules and the antibodies possibly present In the tissue or biological fluid, and the in vitro detection of the antigen-antibody complex possibly formed.

The biological medium is preferably constituted by a human serum.

Any standard procedure may be used to carry out such a detection.

As an example, a preferred method involves immunoenzymatic processes according to the ELISA technique, or immunofluorescent processes, or radioimmunological processes (RIA) or equivalent processes.

Thus, the invention also relates to any polypeptide according to the invention labelled with the aid of a suitable marker of the enzymatic, fluorescent, radioactive, etc. . . type.

Such methods comprise for example the following steps:

deposition of defined amounts of a polypeptide composition according to the invention into the wells of a microtitration plate, introduction into the wells of increasing dilutions of serum requiring diagnosis, incubation of the microplate, repeated rinsings of the microplate, introduction into to the wells of the microplate labelled antibodies against immunoglobulins of the blood, the labelling of such antibodies having been carried out with the aid of an enzyme selected from those which are capable of hydrolyzing a substrate and of modifying the absorption of radiation of this latter at at least one specific wavelength, detection of the amount of substrate hydrolyzed in comparison with a control.

The invention also relates to kits for the in vitro diagnosis of the malaria caused by *P. falciparum* which contain:

polypeptide composition according to the invention, the reagents for constituting the medium appropriate for carrying out the immunological reaction, the reagents making possible the detection of the antigen-antibody complex produced by the immunological reaction. Such reagents may also bear a marker or be capable of being recognized in turn by a labelled reagent, more particularly in the case in which the above-mentioned polypeptide composition is not labelled, a reference tissue or biological fluid devoid of antibodies recognized by the above-mentioned polypeptide composition.

The invention relates to the antibodies themselves formed against the polypeptides of the invention and obtained by of an animal with polypeptides followed by the recovery of the antibodies which have been formed.

It will be obvious that these antibodies are not limited to polyclonal antibodies.

The invention also relates to any monoclonal antibody produced by any hybridoma capable of being formed by standard methods from the spleen cells of an animal, in particular the mouse or the rat immunized against one of the purified polypeptides of the invention, on the one hand, and cells of a suitable myeloma cell line on the other, and of being selected by its capacity to produce monoclonal antibodies recognizing the polypeptide initially used for the immunization of the animals.

The antibodies of the invention can turn out to be particularly useful for the detection of sporozoite in mosquitoes.

The invention also relates to a nucleotide detection probe characterized in that it is constituted by all or part of one of the nucleotide sequences of the invention such as those defined above.

The subject of the invention is more particularly an in vitro diagnostic method for malaria in an individual likely to be infected by *P. falciparum* which comprises the following steps:

if necessary, the prior amplification of the amount of the nucleotide sequences according to the invention likely to be contained in the biological sample taken from the said individual, with the aid of two DNA primers selected in the manner indicated above, the placing in contact of the above-mentioned biological sample with a nucleotide probe such as that defined above under conditions leading to the formation of a hybridization complex formed between the said probe and the said nucleotide sequence, the detection of the above-mentioned hybridization complex possibly formed.

As examples of nucleotide probes of the invention, mention should be made of the nucleotide sequence encoding the peptide sequence of FIG. 1, or also the sequences I and II of FIG. 2.

Finally, the invention opens the way to the development of new vaccinating principles against the malaria resulting from the infection of an individual by *P. falciparum*.

The invention also relates to the Compositions prepared in the form of vaccines containing either the peptide according to the invention or an oligomer of this peptide, or also a conjugate of this peptide or oligomer with a carrier molecule, in combination with a suitable pharmaceutically acceptable vehicle end, if appropriate, with other active vaccinating principles against malaria.

Advantageous pharmaceutical compositions are constituted by injectable solutions, suspensions or liposomes containing an efficient dose of at least one product according to the invention. These solutions, suspensions or liposomes are preferably prepared in a sterilized isotonic aqueous phase, preferably saline Or a glucose solution.

The invention relates more particularly to those suspensions, solutions of liposomes which are suitable for administration by intradermal, intramuscular or subcutaneous injections or also by scarification.

The invention also relates to pharmaceutical compositions Which can be administered by other routes, in particular by the oral or rectal routes or also in the form of aerosols intended to come into contact with mucous membranes, in particular the ocular, nasal, pulmonary or vaginal mucous membranes.

Consequently, it relates to pharmaceutical compositions in which at least one of the products according to the invention is combined with solid or liquid, pharmaceutically acceptable excipients, suited to the constitution of nasal, ocular or oral forms, or with excipients suitable for the constitution of rectal forms of administration, or also with gelatinous excipients for vaginal administration. It also relates to isotonic liquid compositions containing at least one of the conjugates according to the invention, suited to administration to the mucous membranes, in particular nasal or ocular membranes.

Advantageously, the vaccinal compositions according to the invention contain in addition a vehicule such as polyvinyl-pyrrolidone which facilitates the administration of the vaccine. Instead of polyvinyl-pyrrolidone, it is possible to use any other type of adjuvant in the classical sense which was formerly attributed to this expression, i.e. a substance making the absorption of a medicine easier or facilitating its action in the organism. As examples of other adjuvants of this latter type, mention should also be made of carboxymethylcellulose, the hydroxides and phosphates of aluminium or all other adjuvants of this type well known to the person skilled in the art. Finally, they contain, if necessary, an immunological adjuvant, in particular of the muramylpeptide type.

The invention is obviously not limited to the embodiments described above as examples and the person skilled in the art can make modifications to it without in any way departing from the framework of the claims made below; in particular, some of the amino acids occurring in the sequence of the peptides according to the invention can be replaced by isofunctional or isosteric amino acids; for example one or more of the following substitutions can be envisaged:

Glu is substituted by Asp or Gln,

Leu is replaced by Ala, etc. . .

It is of course understood that the peptides which result from such substitutions consist of equivalents of the peptides more especially claimed, provided that they themselves or oligomers or conjugates formed from these peptides exhibit similar immunogenic properties.

The invention also relates more particularly to the "chimeric proteins" which may be obtained by the techniques of genetic engineering, such chimeric proteins containing one or more peptide sequences containing respectively the 87 amino acids of the sequences of the invention, and incorporated into or attached to a peptide fragment other than β-galactosidase. This latter peptide fragment preferably has a molecular weight sufficient to reinforce the immunogenicity of the peptide sequences according to the invention and does not interfere from an immunological point of view with the manifestation of the desired immunogenicity.

Bars derived from European individuals living in endemic zones and following an uninterrupted prophylaxis with medicines directed against the schizonts of the blood stages were selected and tested by using antigens of the sporozoite stage (CS antigens), the hepatic stage (LSA antigen), end blood stages. Most of these sera react with the antigens of all of the stages probably because prophylaxis was interrupted. Three sera taken from individuals who had lived in rural tropical Africa and who had ingested 100 mg of chloroquine per day without interruption for 23 to 26 years did not react with the antigens of the blood stages in the immunofluorescent test (IFA) and the immunoblotting test on nitrocellulose. These three sera, however, possess high titers of antibodies directed against the sporozoites and the proteins of the hepatic stage (IFA dilution 1/3200 and 1/6400, respectively).

One of the three sera just mentioned, of reduced specificity, λgt 11 in the following manner:

1) CONSTRUCTION OF THE GENOMIC DNA BANK OF *Plasmodium falciparum*

The genomic DNA of the clone 96 of the Thai strain Tak9 of *P. falciparum* (Science, 212, 1.37–1.38 (1981)) was isolated by standard techniques.

Samples of 18 μg of DNA of *P. falciparum* were incubated at 15° C. in 50 mM Tris HCl buffer, pH 7.5, 1 mM MnCl$_2$, 20 μg/ml of bovine serum albumin, with amounts of DNAase I (Boehringer Mannheim) of 5 pg for 5 minutes or 3.5 pg for 5 or 10 minutes, respectively. After the addition of 5 mM EDTA (ethylenediamino tetraacetic the DNA samples are pooled and purified by extraction with a mixture of phenol/chloroform/isoamyl alcohol (25 V/24 V/1 V), then by ether. The DNA is concentrated by precipitation with ethanol at −20° C. in the presence of 2.5M ammonium acetate.

45 μg of DNA thus treated were methylated by 180 U of Eco R1 methylase (Biolabs) under the conditions recommended by the supplier, with the further addition of 5 mM (dithiothreitol), for 15 minutes at 37° C. After purification of the DNA as above, 10 μg of DNA were incubated with 40 mM TRis HCl, pH 8.0, 10 mM of ammonium sulfate, 10 mM of 2-mercaptoethanol, 0.5 mM EDTA, 0.05 mM NAD (nicotinamide adenine dinucleotide), 0.1 mM dXTP (comprising the 4 deoxynucleotide triphosphates dATP, dCTP, dGTP and dTTP), in the presence of 10 U T4 DNA polymerase (PL Biochemicals) and 10 U of *E. coli* DNA ligase (Biolabs). The DNA was purified and concentrated as above.

8 μg of DNA were then ligated with 0.4 μg of an Eco R1 adaptor or "linker" (Eco R1 phosporylated adaptors marketed by Biolabs) by means of 4 U T4 DNA ligase (Biotec) in 50 mM Tris HCl buffer, pH 8.0, 10 mM MgCl$_2$, 20 mM DTT, 1 mM ATP, 50 μg/ml bovine serum albumin.

After incubation at 4° C. for 5 hours, 2 U T4 DNA ligase are added and the reaction is continued for 16 hours at 4° C. The tube is then subjected to several cycles of freezing to −80° C./thawing in order to stop the reaction. The DNA is then diluted and the incubation buffer is then adjusted so as to obtain the conditions recommended by the supplier for the use of the Eco R1 enzyme. 100 U of Eco R1 enzyme (Promega Biotec) are added and incubated for 3 hours at 37° C. The reaction is stopped by heating for 10 minutes at 60° C. and the DNA is purified and concentrated as above.

The DNA is resuspended in 100 μl of 50 mM Tris HCl buffer, pH 8.0, 1 mM EDTA, and loaded onto a 5–20% gradient of sucrose prepared in 25 mM sodium acetate, 10 mM EDTA and centrifuged in a Beckman SW 50.1 rotor at 45,000 revolutions per minute for 150 minutes. The fractions are analyzed on agarose gel and those which contain the DNA fragments of sizes included between about 300 pb, and 2,500 pb, are pooled, dialyzed against the 50 mM Tris HCl buffer, pH 8.0, 1 mM EDTA at 4° C. The DNA is concentrated by precipitation with ethanol. About 400 ng of this DNA were ligated with 1 μg of the DNA of the vector gt 11 (*Proc. Natl. Acad. Sci.*, USA, 80, 1194–1198 (1983)) cut by Eco R1 and dephosphorylated (Protoclone of Promega Biotec), in a volume of 10 μl (of 50 mM Tris HCl buffer, pH 8.0, 10 mM MgCL$_2$, 20 mM DTT, 1 mM ATP, 50 μg/ml of bovine serum albumin) by means of 1 U of T4 DNA ligase (Biotec).

The ligation products were encapsulated in vitro in the *E. coli* extracts prepared from the bacterial strains constructed by B. Hohn (*Methods Enzymol.*, 68, 299), according to the technique described by Maniatis et al. (*Molecular Cloning, a laboratory manual*, p. 264, Cold Spring Harbor Laboratory (1982)).

About 7 millions of recombinant bacteriophages were obtained.

2) IMMUNOLOGICAL SCREENING OF THE BANK

The recombinant bacteriophages were spread on a culture medium containing the indicator bacterium Y 1090 at a density of 50,000 phages per 90 mm Petri dish, and incubated at 43° C. for 3 hours.

A nitrocellulose filter (Schleicher and Schuell, BA 85) saturated with 0.01M IPTG isopropyl-β-thiogalactopyranoside (Sigma) is deposited on the dishes which are incubated at 37° C. for 3 hours. On completion of the incubations, the nitrocellulose filters are removed and the Petri dishes are stored at 4° C.

The nitrocellulose filters are placed an a bath of TL buffer: 50 mM Tris HCl, pH 8.0, 150 mM NACl, 5% skimmed milk, 0.05% Tween 20 (Sigmas), The filters are incubated for 15 hours at 4° C. in TL buffer, then twice for 15 minutes at 20° C. They are then incubated for 1 hour with a pool of immune human antisera directed against the antigens of all of the stages of development of *P. falciparum*, treated beforehand in order to deplete it of anti-*E. coli* antibodies according to the method described by Ozaki et al. (*J. Immunol. Methods*, 89, 213–219, 1986). The pool of human antisera was utilized at the dilution of 1/200 in TL buffer. The incubation was done at 20° C. for 1 hour. The filters were washed 4 times with TL buffer, then incubated with anti-human immunoglobulin antibodies conjugated to horseradish peroxidase (Biosys) and iodinated with iodine $^{125}$I for 1 hour at 20° C. After several washings with TL buffer, then with a 50 mM Tris HCl buffer. pH 8.0, 150 mM NaCl, the enzymatic activity of the peroxidase is revealed (Ozaki et al., previously cited), the filters are dried in a stream of air and autoradiographed on Kodak Royal X-OMat AR film with an amplifying screen.

A collection of about 1200 clones of recombinant bacteriophages was constituted by sampling the lyses plaques corresponding to the positive signals. These clones were then subjected to a second cycle of immunological screening, this time by using one of the three human sera previously described and possessing no or few antibodies directed against the erythrocytic forms of *P. falciparum* and a high titer against the hepatic forms of the parasite. This immunological screening was carried out according to the protocol described above. This serum reacts with only 15% of the producer clones of a specific antigen of *P. falciparum* (120 out of 1200 tested) and 60 of the most active clones were selected and studied as follows, The human antibodies which react with the antigenic determinants expressed by the recombinant clones were purified by affinity to the recombinant proteins according to the technique described by Ozaki et al. (previously cited). These specific antibodies were incubated with preparations of parasites at different stages of development (sporozoite, hepatic stage or erythrocytic stages), and the reaction was studied by indirect immunofluorescence and immunoblotting. The recombinant clone to which specific antibodies of the hepatic stage and of the sporozoite stage are retained by affinity and which does express determinants specific to these stages was studied: the clone DG 671 is the clone in question. The antibodies specific for this clone react specifically:

a) on the one hand, with the hepatic schizonts such as may be produced after infection of human or monkey hepatocytes with sporozoites of *P. falciparum*; the localization of the fluorescence was determined to be identical with that considered to be characteristic of the antigens of the hepatic stage;

b) on the other hand, with the surface of the sporozoites of the plasmodial strain NF54, but not that of the parasitic clone 3D7, and with that of 2 of the 8 isolates tested of Thai origin. This reactivity with the surface antigens is demonstrated in the IFI test using so-called "humid" sporozoites or sporozoites in suspension which are attached to a glass slide by the intermediary of a film of Poly-L-Lysine according to the IFI technique described by Druilhe et al (*Infection and Immunity*, (1986) 53, 393–397). The localization of the antigen with which the antibodies react on the surface of the sporozoites has, moreover, been confirmed at the ultra-structural level by revelation of the binding of the antibodies by a second anti-human immunoglobulin antibody coupled to colloidal gold particles. Furthermore, in an IFI test using dried sporozoites fixed in acetone, these antibodies react both with the sporozoites of strain NF54 and with the parasitic clone 3D7. Finally, in an immunoblotting test using proteins extracted by SDS from the sporozoite stages, these antibodies reveal a polypeptide with a molecular weight of 70 kilodaltons in the NF54 strain, the parasitic clone 3D7 and in one of the two positive Thai strains tested. On the other hand, no polypeptide is revealed under the same conditions in the sporozoite extracts from strains with which this IFI test was negative. From these considerations it emerges that the antigen revealed by these antibodies can be present either internally, i.e. in the cytoplasm of the sporozoite stage but not on the surface, or both internally and also at the surface, or is not present.

As a consequence of the properties a) and b) above, the antigen encoded in the nucleic acid sequence of the DG671 clone is designated "SALSA" (Sporozoite and Liver Stage Antigen).

The species- and stage-specificity of the DG671 clone was tested in the following manner. First, it was determined that the same antibodies purified by affinity and which react by IFA (or also which are IFA positive) with the antigens of the hepatic stage and the sporozoites, do not react with the antigens of the blood stages, whether they are tested by means of IFA with the per, sites fixed in acetone or by immunoblotting using proteins extracted with SDS. The antibodies purified by affinity do not react with the antigens of the sporozoite stage of *P. yoelii*, *P. berghei* and *P. vivax* nor with the antigens of the hepatic stage of *P. yoelii*, nor with the hepatic schizonts of *P. vivax* prepared from *Saimiri sciureus* monkeys.

Secondly, the recombinant proteins of DG671 do not react with the sera derived from two patients suffering from malaria (malaria caused by *P. falciparum*) by accidental transfusion and who, by definition thus do not have antibodies to the preceding stages (sporozoites and antigens of the hepatic stage). These proteins do not react with two monoclonal antibodies recognizing the CS tetrapeptide, nor with the sera of mice immunized with the recombinant CS antigens $R_{32}tet32$ (Young et al., *Science*, 228, 957 (1986)), nor with the sera of rabbits immunized with the I end II regions of the CS protein. Furthermore, the recombinant proteins do not react with human antisera directed against *P. vivax* (although the sera had been positive with the hepatic schizonts of *P. vivax*), *P. ovale* and *P. cynomolgi* (*Ann. Soc. Belg. Med. Trop.*, 60, 348 (1980)) when they are tested by the technique of immunodot blots, whereas they are positive with all of the anti-*P. falciparum* human sera tested.

The insert of 261 base pairs of *P. falciparum* was purified and recloned within the plasmid pUC13 (*Nucleic Acids Research*, 9, 309–321 (1981)). The DNA sequence and the genomic organization of the SALSA gene were then determined.

Only one reading frame is in phase with the lacZ gene of β-galactosidase, an expected property since the clone produces a fusion protein which carries the epitopes recognized by human serum. It is composed of a chain of 87 amino acids rich in glutamic acid, lysine and serine but contains neither methionine nor cysteine. Computer analysis of this sequence indicates that it has a high probability of possessing a helical structure in the region of the amino acids included between the positions 10 and 50. Furthermore, no homology between the presently known DNA sequences of *P. falciparum* and the DNA sequence coding for the said protein has been detected by analysis of the Los Alamos and NBRF data banks. On the other hand, a homology of 60.2% exists between the DNA sequence coding for the said SALSA protein and the sequence of a cDNA (complementary DNA) of human hepatic origin. This homology at the nucleotide level is not expressed by a real homology at the peptide level (in fact, the degree of homology here is only 20 to 30%). This is an agreement with the specificity of the SALSA protein for the hepatic stage and sporozoite stage.

Analyses by blotting according to the method of Southern using the fragment of 261 base pairs cloned in pUC 13 indicate that this fragment hybridizes with 2 Eco RI fragments. It is present in the 2 strains of *P. falciparum* examined up to now and localized on chromosome No. 2, The assignment to this location makes it possible to conclude that the corresponding gene is distinct from that for the CS protein of the sporozoites and distinct from that of the LSA antigen previously described.

The studies of hybridization of the DNA of the DG671 clone with the sub-assembly of 120 clones of DNA described previously, and probably coding for antigens of the pre-erythrocytic stage, has shown that the structure of the DG671 clone is unique in this sub-assembly: the DNA of DG671 hybridizes only with itself and does not hybridize with the DNA of the other 119 clones.

As repetitive epitopes appear to be a frequent characteristic of the antigens of *P. falciparum* (*Nature*, 306, 751 (1983); *Nature*, 311, 382 (1984); *Science*, 225, 593 (1984); *Science*, 227, 1595 (1985); *Cell*, 40, 775 (1985)), it is important to emphasize that the SALSA polypeptide does not possess a repetitive structure although it is highly immunogenic in man.

The great prevalence of antibodies against the SALSA antigen is one of its most important characteristics. The presence of antibodies in individuals exposed to malaria and coming from 3 different regions of Africa with respect to the level of transmission of the disease, was studied by immunoblotting on nitrocellulose of the recombinant proteins produced in the colibacilli after separation by electrophoresis. A prevalence varying from 90 to 95% was observed in the individuals studied, depending on the zone. These results are particularly significant if they are compared with the results obtained with other antigens of *P. falciparum*. Thus, in the zone of lowest transmission (the lowest number of infectious bites) the prevalence of antibodies against the CS protein (determined by ELISA with the $R_{32}tet32$ peptide) is only 27% compared with 65% for the antigens of the blood stages (determined by IFI on smears of parasited red cells) or compared with 75% for the LSA antigen (determined by immunoblotting) or compared with 81% for the synthetic LSA (determined by ELISA with the synthetic peptide of 41 amino acids containing 2.5% repetitions of 17 amino acids) or compared with 97% for the SALSA (by immunoblotting).

Table I, hereafter, represents the comparison of the results obtained in the experiment of the same type with immunoblotting with DG671 SALSA antigen, and LSA antigen (WB SALSA, WB LSA) with respect to those obtained by ELISA with the repetitive tetrapeptide of the circumsporozoite protein (ELISA NANB) and by immunofluorescence with hepatic schizont$ of *P. falciparum* (IFA, LS, LS corresponding to "liver stage").

TABLE I

| | AREA OF WEAK ENDEMIA | | | |
|---|---|---|---|---|
| AGE | ELISA NANP | IFA LS | W.B. LSA | W.B. SALSA |
| 0–10 | 0/12 | 12/12 | 8/12 | 11/12 |
| 10–20 | 0/5 | 5/5 | 4/5 | 5/5 |
| >20 | 7/13 | 13/13 | 12/13 | 11/13 |
| total | 7/30 | 30/30 | 24/30 | 27/30 |

In view of these results and of the non-uniform presence of the epitopes contained in the recombinant SALSA protein in the sporozoites of various isolates, it is possible to put forward the hypothesis that the epitopes are more frequently expressed at the hepatic stage than at the sporozoite stage.

The analysis of the conformation of the amino acid sequence according to the technics of Chou et al ("Prediction of Protein Conformation,"*Biochemistry*, 13, 222 (1974)) enables to predict that three areas of the SALSA molecules have a strong tendancy to be arranged in the shape of a helix α, one being comprised between the amino acids 25 to 51, the two others being comprised between the amino acids 52 to 87. Consequently, synthetic peptides representing the following sequence have been prepared:

1-SAEKKDEKEASEQGEESHKKENSQESA designated SALSA1

2-NGKDDVKEEKKTNEKKDDGKDDKVQEKVLEKSPKEF designated SALSA2

They have been purified and used in various immunological tests.

In ELISA, sera of subjects living in area of weak endemia react specifically with each of these peptides. In three groups of individuals belonging to all the classes of ages, the prevalence of anti-SALSA1 or 2 antibodies vary from 25 to 60%. There is a non drastic parallelism of the reponses to the recombinant DG671 protein. The study of the return of the blood to positive (reapparence of parasites) after drastic treatment of malaria and responses to the peptides SALSA1 and 2 have been carried out according to the following manner: a group of 250 individuals has received a drastic treatment with chloroquine (dosage=25 mg/kg, enough to eliminate all the parasites which are present) in order to destroy any parasitemia existing.

They have then been followed clinically and parasitologically for three months of the season of transmission of malaria by Anophales mosquitoes to detect the re-emergence of parasites in the blood.

Two groups of 40 individuals have been selected, the ones having presented no parasitemia during the length of the time that they were followed, the others having a positive blood test for *P. falciparum* (Smear and thick drop coloured with giemsa).

For the subjects, the blood test of which has remained negative, the prevalence and the average titers of antibodies with respect to the SALSA1 and 2 peptides are substantially higher than the ones having presented a parasitemia.

On the contrary, the prevalence of the ones who answer and the antibody rates with respect to a control antigen, the repetitive tetrapeptide NANE of the circumsporozoite protein, are identical in the two groups.

These results suggest that the immuneresponse with respect to PG671-SALSA interfers with the development of the intra-hepatic multiplying stage of the parasite.

On the contrary, there is no indication that the response to the circumsporozoite protein can have the same effect, In other words, these results suggest that the development of an immunity against SALSA molecule can have a protecting effect for man against the infection of *Plasmodium falciparum*.

The proliferative response of lymphocytes of subject exposed to malaria has been studied with respect to peptidic antigen SALSA 1. The results show that this peptidic sequence comprises an epitope which is recognized by the T-lympocytes of an important ratio of the individuals who have been exposed.

The lymphocytes CD4+ of 7 out 10 individuals who have been studied, have proliferated in the presence of SALSA1 peptide (1 and 10 µg/ml) and in the presence of interleukin-2 (IL-2). The ratio of proliferation with respect to IL-2 control alone is higher than 10. This result shows that the individuals who are genetically able to respond to the SALSA1 peptide are more frequently met in endemic area then those able to respond to the epitopes T of the circumsporozoite. In other words, the epitopes T of SALSA polypeptide are genetically less restrained than the ones of the circumsporozoite protein.

The invention also relates to the recombinant nucleic acids containing the sequence coding for the SALSA polypeptide, as well as the micro-organisms, in particular the *E. coli* bacteria transformed by those recombinant nucleic acids and capable of expressing the said polypeptide.

The invention relates to these nucleic acid sequences or equivalent sequences which can be synthesized and which code for the same amino acids.

It will be immediately apparent to the person skilled in the art that in these sequences, some of the nucleotides can be replaced by others by virtue of the degeneracy of the genetic code without the encoded peptides being modified. All of these nucleic acid sequences as well as those which code for polypeptides which differ from the ones already mentioned by one or more amino acids without their intrinsic immunogenic activity being modified in a similar manner, form part of the invention. Naturally, the same is true of the nucleotide sequences which can be reconstituted and which are capable of coding for oligomers such as those which were defined above. The monomeric units are linked directly end to end or by the intermediary of peptide sequences without effect on the immunogenic properties of the oligomers so formed.

Finally, the invention relates to the vectors modified by these micro-organisms, these vectors being naturally provided with elements for regulation and termination preceding and following the above-mentioned nucleic acid sequences, which will make possible the expression of these latter in competent cell organisms.

Bacteria acting as host to the above-mentioned clone DG671 have been deposited with the Collection Nationale de Cultures de Microorganismes ("C.N.C.M."), Institut Pasteur, 28 rue du Docteur Roux, 75724 PARIS CEDEX 15, on Mar. 31, 1989 under the Accession No. I-855.

We claim:

1. A peptide having 10 to 87 amino acids of the following sequence:

Glu-Phe-Arg-Val-Ser-Thr-Ser-Asp-Thr-Pro-Gly-Gly-Asn-Glu-Ser-Ser-Ser-Ala-Ser-Pro-Asn-Leu-Ser-Gly-Ala-Arg-Glu-Lys-Lys-Asp-Glu-Lys-Glu-Ala-Ser-Glu-Gln-Gly-Glu-Glu-Ser-His-Lys-Lys-Glu-Asn-Ser-Gln-Glu-Ser-Ala-Asn-Gly-Lys-Asp-Asp-Val-Lys-Glu-Glu-Lys-Lys-Thr-Asn-Glu-Lys-Lys-Asp-Asp-Gly-Lys-Thr-Asp-Lys-Val-Gln-Glu-Lys-Val-Leu-Glu-Lys-Ser-Pro-Lys-Glu-Phe which peptide is recognized by antibodies recognizing the sporozoite and hepatic stages of *Plasmodium falciparum* and is not recognized by antibodies recognizing the blood stage of *Plasmodium falciparum.*

2. The peptide according to claim 1, wherein said peptide comprises the 87 amino acids of said sequence.

3. The peptide according to claim 1, comprising the following sequence:

Ala-Arg-Glu-Lys-Lys-Asp-Glu-Lys-Glu-Ala-Ser-Glu-Gln-Gly-Glu-Glu-Ser-His-Lys-Lys-Glu-Asn-Ser-Gln-Glu-Ser-Ala.

4. The peptide according to claim 1, comprising the following sequence:

Asn-Gly-Lys-Asp-Asp-Val-Lys-Glu-Glu-Lys-Lys-Thr-Asn-Glu-Lys-Lys-Asp-Asp-Gly-Lys-Thr-Asp-Lys-Val-Gln-Glu-Lys-Val-Leu-Glu-Lys-Ser-Pro-Lys-Glu-Phe.

5. An immunogenic composition comprising one or more peptides according to claim 1, and a pharmaceutically acceptable vehicle.

6. A composition capable of inhibiting the development of the sporozoite and hepatic stages of *Plasmodium falciparum* comprising a pharmaceutically effective amount of one or more peptides according to claim 1.

7. An in vitro diagnostic method for the detection of the presence or absence of antibodies indicative of malaria caused by *Plasmodium falciparum,* which bind with a peptide according to claim 1, to form an immune complex, comprising:

contacting a peptide according to claim 1 with a biological sample for a time and under conditions sufficient for said peptide and antibodies in the biological sample to form immune complex, and detecting the presence or absence of immune complex.

8. A diagnostic kit for the detection of the presence or absence of antibodies indicative of malaria caused by *Plasmodium falciparum,* comprising:

a peptide according to claim 1;

a reagent to detect peptide-antibody immune complex;

a biological reference sample lacking antibodies that immunologically bind with said peptide; and a comparison sample comprising antibodies which can specifically bind to said peptide;

wherein said peptide, reagent, biological reference sample, and comparison sample are present in an amount sufficient to perform said detection.

9. The diagnostic kit of claim 8, wherein the formation of immune complex is detected by employing immunological labels selected from the group consisting of radioisotopes, immunoenzymes, and immunofluorescent labels.

* * * * *

UNITED STATES PATENT AND TRADEMARK OFFICE
CERTIFICATE OF CORRECTION

PATENT NO. : 5,690,941

DATED : November 25, 1997

INVENTOR(S) : Pierre Druilhe and Claudine Guerin-Marchand

Page 1 of 2

It is certified that error appears in the above-indentified patent and that said Letters Patent is hereby corrected as shown below:

IN THE DRAWINGS:

Sheets 1 of 4:

delete: The Fig.1 in its entirety and insert therefor

--Glu-Phe-Arg-Val-Ser-Thr-Ser-Asp-Thr-Pro-Gly-Gly-Asn-
Glu-Ser-Ser-Ser-Ala-Ser-Pro-Asn-Leu-Ser-Gly-Ala-Arg-
Glu-Lys-Lys-Asp-Glu-Lys-Glu-Ala-Ser-Glu-Gln-Gly-Glu-
Glu-Ser-His-Lys-Lys-Glu-Asn-Ser-Gln-Glu-Ser-Ala-Asn-
Gly-Lys-Asp-Asp-Val-Lys-Glu-Glu-Lys-Lys-Thr-Asn-Glu-
Lys-Lys-Asp-Asp-Gly-Lys-Thr-Asp-Lys-Val-Gln-Glu-Lys-
Val-Leu-Glu-Lys-Ser-Pro-Lys-Glu-Phe
Fig. 1--;

delete "FIG. 3" and insert therefor --FIG.2--.

Sheet 2 of 4:

delete Fig. 2 in its entirety.

Figure 4:
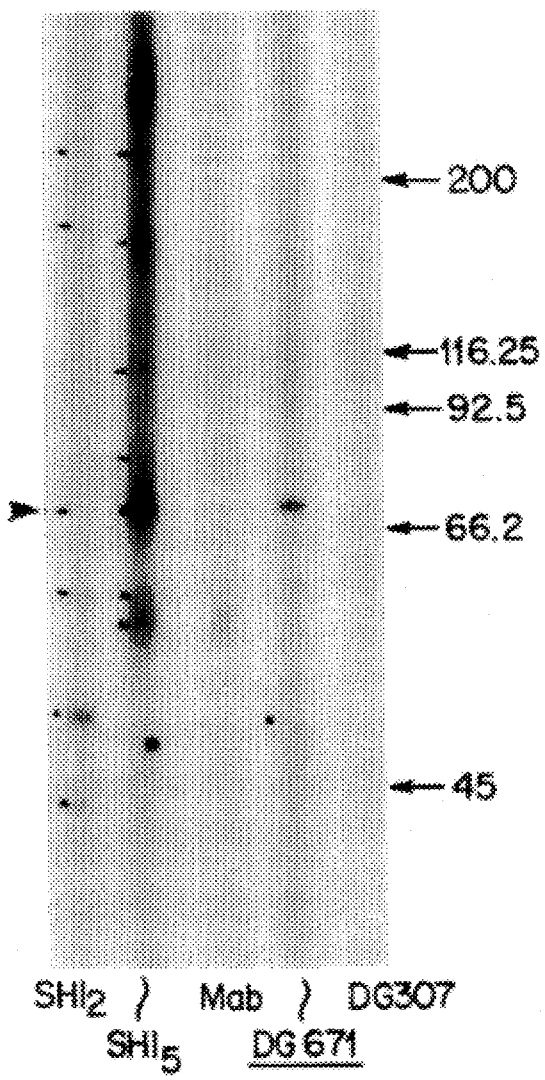
FIG. 4 represents the localization of the sporozoite surface protein SALSA: electron microscopy labeling of cuts of sporozoite (NF54 strain) by antibodies anti-SALSA (DG 671) revealed by a second antibody labelled with colloidal gold. Controls: total serum SH12 and anti-SALSA antibody (control).

Sheet 3 of 4:

delete "FIG. 4" and insert therefor --FIG. 3--.

UNITED STATES PATENT AND TRADEMARK OFFICE
CERTIFICATE OF CORRECTION

PATENT NO. : 5,690,941  
DATED : November 25, 1998  
INVENTOR(S) : Pierre Druilhe and Claudine Guerin-Marchand Page 2 of 2

Figure 5A:
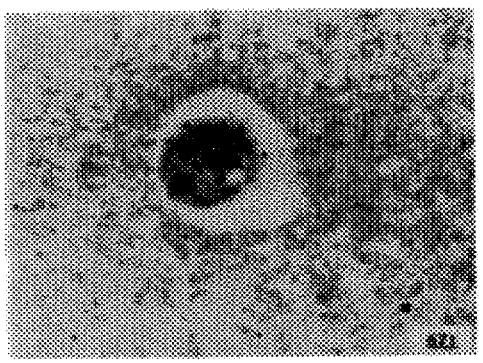
Figure 5B:
Figure 5C:
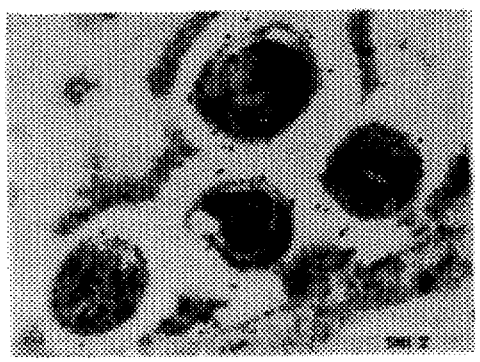
Figure 5D:
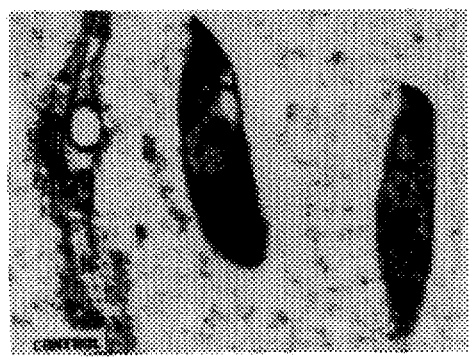

It is certified that error appears in the above-indentified patent and that said Letters Patent is hereby corrected as shown below:

Sheet 4 of 4:

delete "FIG. 5A" and insert therefor --FIG. 4A--;

delete "FIG. 5B" and insert therefor --FIG. 4B--;

delete "FIG. 5C" and insert therefor --FIG. 4C--;

delete "FIG. 5D" and insert therefor --FIG. 4D--.

Signed and Sealed this

Fourth Day of August, 1998

Attest:

BRUCE LEHMAN

*Attesting Officer*   *Commissioner of Patents and Trademarks*